United States Patent [19]

Henrick

[11] Patent Number: 4,697,033

[45] Date of Patent: Sep. 29, 1987

[54] CARBAMIC AND CARBAMOTHIOIC ACID ESTERS AS PESTICIDES

[75] Inventor: Clive A. Henrick, Palo Alto, Calif.

[73] Assignee: Sandoz Ltd., Basel, Switzerland

[21] Appl. No.: 813,182

[22] Filed: Dec. 24, 1985

[51] Int. Cl.[4] .................. C07C 149/40; C07C 125/06; C07C 155/02; C07C 119/20
[52] U.S. Cl. ........................................ 558/233; 560/9; 560/17; 560/29; 560/115; 560/161; 560/163; 560/164; 560/24; 558/231; 558/234; 558/235; 558/236; 558/240; 558/241; 558/242
[58] Field of Search ....................... 560/9, 17, 29, 115, 560/161, 163, 164; 558/231, 233, 234, 235, 236, 240, 241, 242, 4, 5, 8

[56] References Cited

U.S. PATENT DOCUMENTS 4,122,111 10/1978 Scavino .............................. 558/233

FOREIGN PATENT DOCUMENTS 0129513 6/1984 European Pat. Off. ............ 558/242
0138181 10/1984 European Pat. Off. ............ 558/242

OTHER PUBLICATIONS

Fukuto, Pesticide Synthesis through Rational Approaches, ACS Symposium Series.

*Primary Examiner*—Henry R. Jiles
*Assistant Examiner*—Robert C. Whittenbaugh
*Attorney, Agent, or Firm*—Jacqueline S. Larson

[57] ABSTRACT

Certain novel derivatives of carbamates and their use for the control of pests.

26 Claims, No Drawings

CARBAMIC AND CARBAMOTHIOIC ACID ESTERS AS PESTICIDES

This invention relates to derivatives of carbamates, and their use for the control of pests, and in particular for the control of insects.

More particularly, the compounds of the present invention are represented by the following formula:

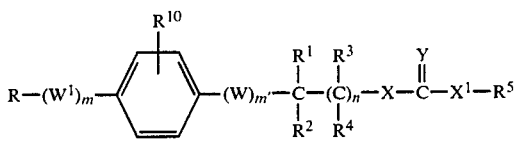
(A)

wherein,
each of m and m' is independently zero or one;
n is zero, one, two or three;
n' is zero, one or two;
n" is zero, one, two or three;
W is oxygen, sulfur, $NR^6$, $CR^3R^4$ or carbonyl;
$W^1$ is oxygen, sulfur, $NR^6$, $CR^3R^4$, carbonyl, sulfinyl or sulfonyl;
each of X and $X^1$ is oxygen, sulfur or $NR^7$; provided that one of X or $X^1$ must be $NR^7$, while the other of X or $X^1$ is oxygen or sulfur;
$X^2$ is oxygen or sulfur;
Y is oxygen, sulfur or $NR^6$;
Z is oxygen or sulfur;
R is hydrogen, lower alkyl, lower alkenyl, lower alkynyl, lower haloalkyl, lower haloalkenyl, lower haloalkynyl, lower alkoxyalkyl, lower alkylthioalkyl, cycloalkyl, halocycloalkyl, cycloalkylalkyl, heterocycloalkyl, or heterocycloalkylalkyl;
each of $R^1$, $R^2$, $R^3$, $R^4$, and $R^6$ is independently hydrogen or lower alkyl;
$R^5$ is lower alkyl, lower alkenyl, lower alkynyl, lower haloalkyl, lower haloalkenyl, lower haloalkynyl, cycloalkyl, cycloalkylalkyl, phenyl or substituted phenyl;
$R^7$ is selected from the groups:

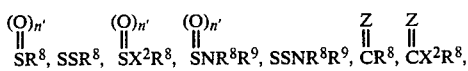

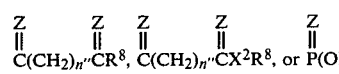

$R^8$ is hydrogen, lower alkyl, lower haloalkyl, lower cyanoalkyl, or substituted or unsubstituted aryl;
$R^9$ is lower alkyl, aryl, alkoxycarbonyl, substituted or unsubstituted aryloxycarbonyl, alkoxycarbonylalkyl, lower alkylsulfonyl, alkylaminosulfonyl, dialkylaminosulfonyl or the group

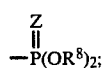

and
$R^{10}$ is hydrogen, lower alkyl, lower haloalkyl or halogen.

In the description hereinafter and the claims, each of m, m', n, n', n", R-$R^{10}$, W, $W^1$, X, $X^1$, $X^2$, Y and Z is as defined above, unless otherwise specified.

The compounds of the present invention of formula (A) can be prepared by methods known in the art, such as those described in European Patents 138,181 and 129,513 and by T. R. Fukuto, "Propesticides," *Pesticide Synthesis Through Rational Approaches* (ACS Symposium Series 255, American Chemical Society, 1984), and as outlined below:

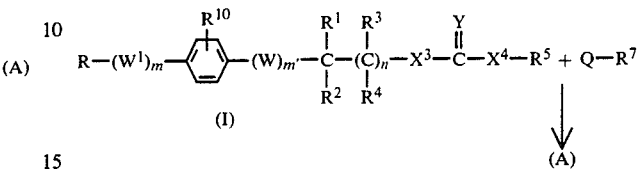

In the above synthesis, a carbamate (I), where either $X^3$ or $X^4$ is NH and the other is oxygen or sulfur, is reacted with a halide Q-$R^7$ (Q is chlorine, bromine or iodine) in an organic solvent such as N-methylpyrrolidone, dimethylformamide or tetrahydrofuran and at a reaction temperature of between 0° and 140°, preferably at between 10° and 110°, in the presence of a base such as potassium carbonate, pyridine or triethylamine. Alternatively, the salt of (I) is prepared with sodium hydride and this salt is reacted with the halide Q-$R^7$.

The starting compound (I) can be prepared by methods known in the art, such as those described in U.S. Pat. Nos. 4,080,470 and 4,215,139 and European Pat. No. 98,800 for example, and as outlined below:

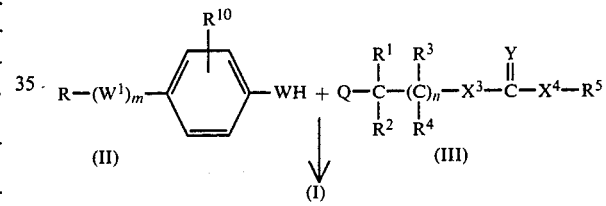

In the above synthesis, a phenol, phenylthiol or aniline of formula II is reacted with a halide of formula III (Q is chlorine, bromine or iodine) in an organic solvent such as N-methylpyrrolidone, dimethylformamide or tetrahydrofuran and at a reaction temperature of between 0° and 140°, preferably at between 10° and 110°, in the presence of a base such as potassium carbonate or sodium hydroxide. Alternatively, the salt of (II) is prepared with sodium hydride and this salt is reacted with a halide of formula III.

Alternatively, a phenol, phenylthiol or aniline of formula IV is reacted with sodium hydride to form the salt and this salt is then reacted with a halide or a mesylate R-$Q^1$ (where $Q^1$ is halogen or mesyl), in an organic solvent and at room temperature or above to give a compound of formula I.

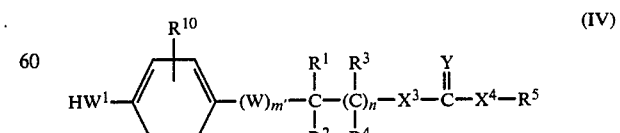

In a third synthetic method, an alcohol, thiol or amine (V), or a salt thereof, is reacted with a halide (VI) following the same general parameters and conditions as described above.

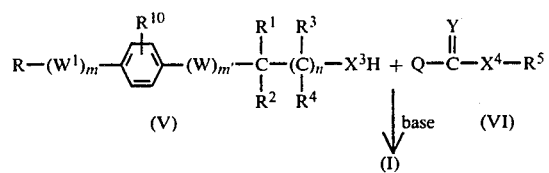

(V)  (VI)

↓ base (I)

When $X^4$ is NH and $Y'$ is oxygen or sulfur, the compounds of the present invention can be prepared from an alcohol, thiol or amine (V) and an isocyanate or isothiocyanate (VII).

$$(V) + Y'=C=N-R^5$$

(VII)

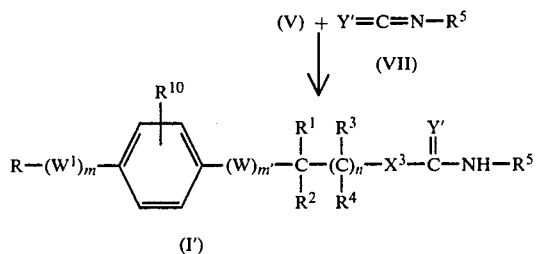

(I')

In another synthetic method, a halide of formula (VIII) is reacted with an alcohol, thiol, or amine (IX), following the above procedures.

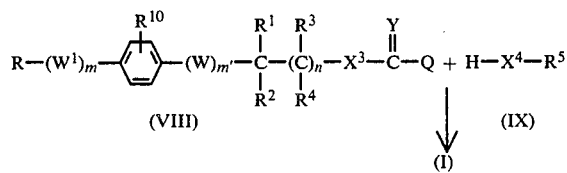

(VIII)  (IX)

↓

(I)

Where m' is one, W is carbonyl and $X^3$ is NH, the compounds of the present invention are prepared as follows:

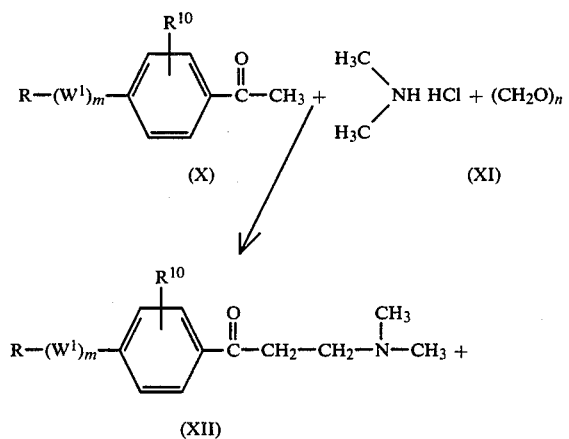

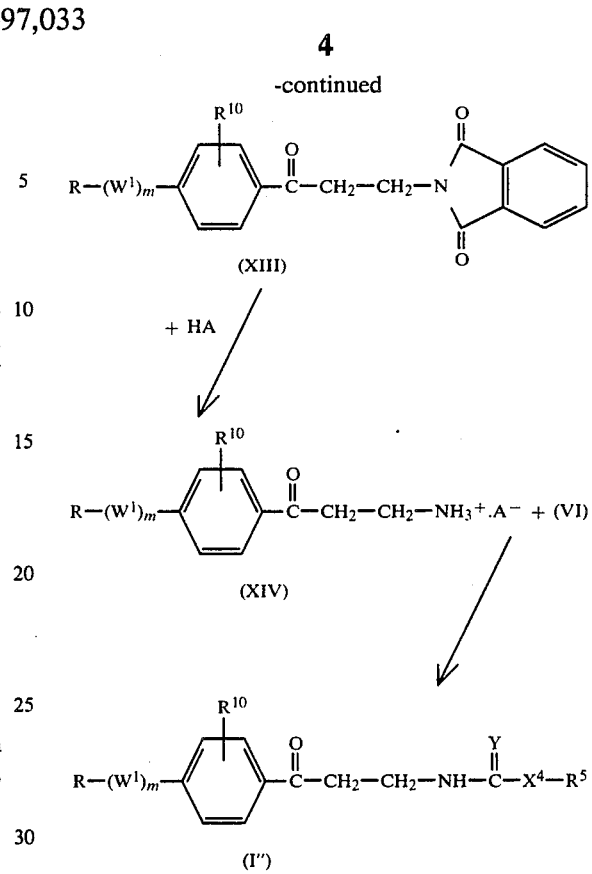

(XIII)

+ HA

↓

(XIV)

↓

(I'')

In the above synthesis, a 4-substituted acetophenone (X) is treated with dimethylamine hydrochloride (XI) and p-formaldehyde in a solvent such as 95% ethanol and under acidic conditions to give the β-aminopropiophenone (XII) which is reacted with phthalimide to give the β-phthalimidopropiophenone (XIII). Compound (XIII) is saponified under acidic conditions to give the β-aminopropiophenone acid salt, which is then reacted with a halide (VI) following the general parameters and conditions described previously to give the final compound (I'').

Compounds of formula A where $W^1$ is sulfinyl are prepared by reacting a compound of formula A where $W^1$ is sulfur with one equivalent of sodium periodate or m-chloroperbenzoic acid in a solvent such as methanol or methylene chloride. Compounds where $W^1$ is sulfony are prepared in the same manner, except that two equivalents of m-chloroperbenzoic acid are used. Alternatively, either hydrogen peroxide in warm acetic acid or excess hydrogen peroxide with selenium dioxide is used as a oxidant.

The compounds of the present invention of formula A can have one or more assymetric carbon atoms. The present invention includes each of the optical isomers and racemic mixtures thereof. In the examples hereinafter, unless otherwise specified, the compound prepared is a racemic mixture.

The compounds of the present invention of formula A are useful pest control agents, particularly for the control of insects, mites and ticks. The utility of these compounds as pest control agents is believed to be attributable to their juvenile hormone activity. They are preferably applied to the immature pest, namely during the embryo, larval or perpupal state, in view of their effect on metamorphosis and otherwise abnormal development leading to death and inability to reproduce.

These compounds can be effective control agents for insects of, for example, the orders Lepidoptera, Hemiptera, Homoptera, Coleptera, Diptera, Orthoptera, and Siphonaptera, and other insects, as well as mites and ticks of the class Acari, including mites of the families Tetranychidae or Tarsonemidae and ticks of the families Argasidae and Ixodidae. The compounds can be applied to the pest or its habitat in a pest controlling amount, usually of the order of 0.1 μg to 100 μg per insect, mite or tick.

In the use of the compounds of formula A for combatting pests, a compound of formula A, or mixtures thereof, can be combined with a carrier substance for application to the pest or its habitat. The carrier can be liquid or solid and include adjuvants such as wetting agents, dispersing agents and other surface active agents. The compounds can be used in formulations such as wettable powders, solutions, dusts, granules, emulsifiable concentrates and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to 90.0 percent, by weight. Generally, a concentration of less than 25 percent of the active compound is employed.

The compounds of formula A can be combined with a cyclodextrin to make a cyclodextrin inclusion complex for application to the pest or its habitat. The compounds of the present invention can be used in combination with other pesticides such as the synthetic pyrethroids, carbamates, phosphates and insect growth regulators, or with insect attractants.

The following terms, wherever used in the description herein and in the appended claims, have the meaning defined below, unless otherwise specified hereinafter.

The term "lower alkyl" refers to an alkyl group, straight or branched, having a chain length of one to ten carbon atoms. The term "lower haloalkyl" refers to a lower alkyl group substituted with one to six halogen atoms. The term "lower cyanoalkyl" refers to a lower alkyl group substituted with a cyano group.

The term "lower alkenyl" refers to an alkenyl group, straight or branched, having a chain length of two to eight carbon atoms and one or two ethylenic bonds. The term "lower haloalkenyl" refers to a lower alkenyl group substituted with one to six halogen atoms.

The term "lower alkynyl" refers to an alkynyl group, straight or branched, having a chain length of two to eight carbon atoms and one or two acetylenic bonds. The term "lower haloalkynyl" refers to a lower alkynyl group substituted with one to six halogen atoms.

The term "lower alkoxyalkyl" refers to an alkyl group substituted at one of the carbon atoms by an alkoxy group, straight or branched, the total number of carbon atoms being not greater than ten.

The term "lower alkylthioalkyl" refers to a lower alkyl group substituted at one of the carbon atoms by an alkylthio group, straight or branched, the total number of carbon atoms being not greater than ten.

The term "cycloalkyl" refers to a cycloalkyl group of three to eight cyclic carbon atoms. The term "cycloalkylalkyl" refers to a cycloalkyl group wherein one of the hydrogen atoms is replaced by a lower alkyl group, the total number of carbon atoms being from four to twelve. The term "halocycloalkyl" refers to a cycloalkyl group substituted with one to six halogen atoms.

The term "heterocycloalkyl" refers to a heterocycloalkyl group, saturated or unsaturated, of two to six carbon atoms and one to three atoms selected from nitrogen, oxygen or sulfur. The term "heterocycloalkylalkyl" refers to a heterocycloalkyl group wherein one hydrogen is replaced by a lower alkyl group, the total number of carbon atoms being from three to twelve.

The term "substituted phenyl" refers to a phenyl group substituted at one, two or three of the ring carbon atoms with a group selected from lower alkyl, lower haloalkyl, lower alkoxy, lower haloalkoxy, halogen, nitro, cyano and lower alkylthio.

The term "aryl" refers to a phenyl group, a benzyl group or a phenethyl group. The term "substituted aryl" refers to a phenyl group, benzyl group or a phenethyl group substituted at one, two or three of the ring carbon atoms with a group selected from lower alkyl, lower haloalkyl, lower alkoxy, lower haloalkoxy, halogen, nitro, cyano and lower alkylthio.

The term "alkoxycarbonyl" refers to an alkoxycarbonyl group, straight or branched, of two to eleven carbon atoms.

The term "alkoxycarbonylalkyl" refers to a lower alkyl group substituted at one of the carbon atoms by an alkoxycarbonyl group, the total number of carbon atoms being not greater than twelve.

The term "aryloxycarbonyl" refers to a phenoxycarbonyl group or a benzyloxycarbonyl group. The term "substituted aryloxycarbonyl" refers to a phenoxycarbonyl group or a benzyloxycarbonyl group substituted at one, two or three of the ring carbon atoms with a group selected from lower alkyl, lower haloalkyl, lower alkoxy, lower haloalkoxy, halogen, nitro, cyano and lower alkylthio.

The term "lower alkylsulfonyl" refers to an alkylsulfonyl group, straight or branched, of one to eight carbon atoms.

The term "alkylaminosulfonyl" refers to an aminosulfonyl group wherein one of the hydrogen atoms attached to the nitrogen atom is replaced by a lower alkyl group. The term "dialkylaminosulfonyl" refers to an aminosulfonyl group wherein each of the two hydrogen atoms is replaced by a lower alkyl group.

Preferred embodiments of the present invention are represented by the following formulas (B) and (C):

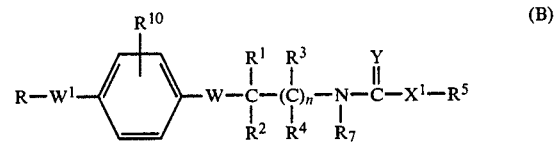

(B)

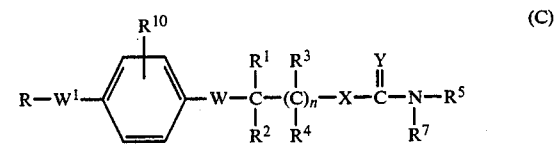

(C)

Also included within the scope of the present invention are bis carbamyl sulfides and disulfides of the following formulas (D) and (E), wherein each of X and $X^1$ is oxygen or sulfur, the values of the other substituents are as defined above and $m''$ is one or two:

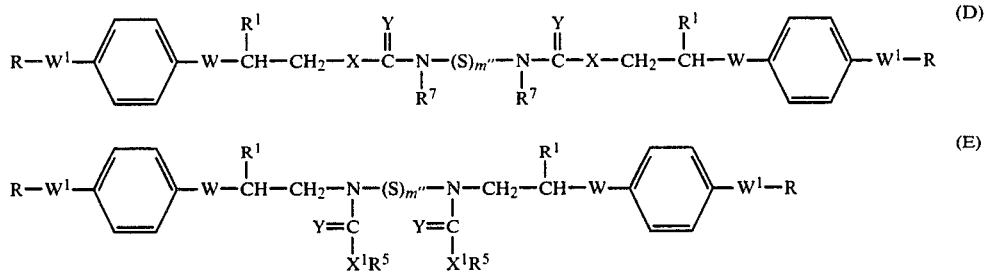

The compounds of formula (D) or (E) where m″ is one can by synthesized by reacting the starting carbamate (I) with either sulfur dichloride (SCl₂) or sulfur monochloride (S₂Cl₂) in the presence of an acid acceptor and with or without a solvent.

The compounds of formula (D) or (E) where m″ is two can be prepared following the procedure in U.S. Pat. No. 4,315,928, wherein an appropriate isocyanate or isothiocyanate (XV) is reacted with hydrogen fluoride in the presence of sulfur monochloride to give the carbamoyl fluoride (XVI) which is subsequently reacted with the appropriate alcohol or thiol R″XH.

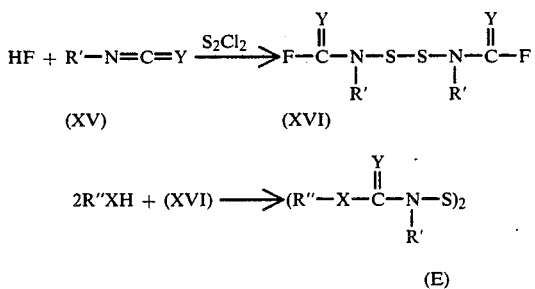

The following examples are provided to illustrate the practice of the present invention. Temperature is given in degrees Centigrade. RT means room temperature.

EXAMPLE 1

4-(1-Methylpropoxy)phenol (6.92 g, 41.6 mmol), ethylene carbonate (7.34 g, 83.2 mmol) and dimethylformamide (DMF; 45 ml) are mixed under N₂. With stirring, the mixture is degassed (3X) by alternate application of vacuum and N₂. Potassium carbonate (11.51 g, 83.2 mmol) is then added, under N₂, and the mixture is heated at 90° for 27 hours. The reaction mixture is then poured into ice water and 10 ml of 40% potassium carbonate solution is added to increase the pH to 13. The aqueous phase is extracted with ether (3X) and the organic layers are washed with 40% KOH, with water until neutral and with brine, dried, filtered and the solvent evaporated to give 2-[4-(1-methylpropoxy)phenoxy]ethanol.

Dibutylin diacetate (0.004 ml) is added to a solution of the above alcohol (0.42 g, 2.0 mmol) in 1.5 ml of DMF and the mixture is chilled in an ice bath. Ethyl isocyanate (0.18 ml, 2.2 mmol) is then added and the mixture is allowed to warm slowly to RT. The mixture is then poured into ether and water containing 10% potassium dihydrogen phosphate. The aqueous phase is extracted with ether, and the combined organic phases are washed with water and with brine, dried, filtered and the solvent is removed in vacuo to give O-2-[4-(1-methylpropoxy)phenoxy]ethyl N-ethylcarbamate.

Methyl oxalyl chloride (1.07 ml, 11.60 mmol) is added rapidly to O-2-[4-(1-methylpropoxy)phenoxy]ethyl N-ethylcarbamate (2.04 g, 7.26 mmol) in dichloroethane (20 ml) at RT. The reaction mixture is slowly warmed to gentle reflux and heated for 19 hours. After the reaction is complete, the mixture is cooled to RT, the solvent is removed under vacuum, and the residue is dissolved in chloroform. The chloroform layer is washed with water and with brine, and dried over calcium sulfate. The mixture is filtered and solvent removed from the filtrate to give, after purification, O-2-[4-(1-methylpropoxy)phenoxy]ethyl N-ethyl-N-methoxyalylcarbamate, MS m/e 368 (M+ +H), (compound 1, Table A).

nmr (CDCl₃) δ centered at 1.08 (m, 9H), centered at 3.79 (q, 2H), 3.87 (s, 3H), centered at 4.18 (m, 3H), centered at 4.55 (m, 2H) and 6.83 ppm (s, 4H).

EXAMPLE 2

Potassium t-butoxide (30.6 g, 275.0 mmol) is added to a solution of 4-methoxybenzenethiol (30.0 ml, 250.0 mmol) in 250 ml of DMF. The mixture is heated at 80° until homogeneous, after which 2-bromobutane (30.0 ml, 275.0 mmol) in 30 ml of DMF is added dropwise over approx. 30 min. The mixture is stirred at 60° overnight, after which it is cooled and is then poured into water and the aqueous phase is extracted with ether (3X). The combined ether extracts are washed with water, with 5% sodium hydroxide, with water and with brine, dried, and the solvent removed to give 4-(1-methylpropylthio)anisole.

To sodium hydride (6.6 g, 275 mmol; prewashed with pentane) in 100 ml of DMF, under N₂ and at 5°, is slowly added ethyl mercaptan (41.0 ml, 550.0 mmol) in 50 ml of DMF. This mixture is stirred for 1.5 hours, after which is added 4-(1-methylpropylthio)anisole (46.0 g, 250.0 mmol) and DMF. The mixture is heated to 150° with stirring overnight. After cooling to 20°, 10% aqueous sulfuric acid is added and the mixture is extracted with ether. The combined organic layers are washed with water and extracted with 5% NaOH. The aqueous portion is reacidified with conc. sulfuric acid and extracted with ether. The combined ether extracts are washed with water and with brine, dried and the solvent removed to give 4-(1-methylpropylthio)phenol.

A mixture of ethylene carbonate (41.08 g, 460.0 mmol) and potassium carbonate (63.57 g, 460.0 mmol) in 100 ml of DMF is heated to 110° and 4-(1-methylpropylthio)phenol (40.19 g, 230.0 mmol) in 100 ml DMF is slowly added dropwise with stirring. The mixture is stirred at 100° for 8 hours. Water is added to the cooled reaction mixture and the aqueous phase is extracted with ether. The combined organic layers are washed with 5% NaOH, with water and with brine, dried and the solvent removed to give 2-[4-(1-methylpropylthio)phenoxy]ethanol.

A mixture of the above alcohol (2.16 g, 10.0 mmol) and potassium carbonate (1.66 g, 12.0 mmol) in 10 ml of DMF is cooled to 5° and ethyl isothiocyanate (1.10 ml, 12.0 mmol) in 10 ml of DMF is added dropwise. After addition is complete, the mixture is allowed to warm to RT and is stirred at RT overnight. Water is added and the aqueous phase is extracted with ether. The combined organic layers are washed with water and brine, dried, and the solvent removed, and the residue is purified by column chromatography to give O-2-[4-(1-methylpropylthio)phenoxy]ethyl N-ethylthiocarbamate.

Following the procedure of Example 1, methyloxalyl chloride and O-2-[4-(1-methylpropylthio)phenoxy]ethyl N-ethylthiocarbamate are reacted together to give O-2-[4-(1-methylpropylthio)phenoxy]ethyl N-ethyl-N-methoxalylthiocarbamate, MS m/e 400 (M++H) (compound 2, Table A).

nmr (CDCl$_3$) δ centered at 1.13 (m, 9H), centered at 3.03 (m, 1H), 3.80 (s, 3H), centered at 4.35 (m, 4H), centered at 4.85 (m, 2H), centered at 6.84 (d, 2H), and centered at 7.41 ppm (m, 2H).

EXAMPLE 3

Following the procedure of Example 2, 2-[4-(1-methylpropylthio)phenoxy]ethanol (2.16 g, 10.0 mmol) is reacted with ethyl isocyanate (1.5 ml, 18.0 mmol) to give O-2-[4-(1-methylpropylthio)phenoxy]ethyl N-ethylcarbamate.

Alternatively, the procedure in Example 1 can be used to prepare the above N-ethylcarbamate.

Following the procedure of Example 1, O-2-[4-(1-methylpropylthio)phenoxy]ethyl N-ethylcarbamate and methyloxalyl chloride are reacted together to give O-2-[4-(1-methylpropylthio)phenoxy]ethyl N-ethyl-N-methoxalylcarbamate, MS m/e 384 (M++H) (compound 3, Table A).

nmr (CDCl$_3$) δ centered at 1.10 (m, 9H), centered at 3.03 (m, 1H), centered at 3.81 (q, 2H), 3.87 (s, 3H), centered at 4.23 (m, 2H), centered at 4.55 (m, 2H), centered at 6.83 (d, 2H) and centered at 7.40 ppm (m, 2H).

EXAMPLE 4

Following the procedures of Example 1, each of the phenols under column I is reacted with ethylene carbonate to give the corresponding substituted-phenoxyethanol, which is then reacted with ethyl isocyanate to give the corresponding carbamate under column II.

I a. 4-(3-methyl-2-butenoxy)phenol
b. 4-(1-methylbutoxy)phenol
c. 4-(2-methylbutoxy)phenol
d. 4-(2-chloro-2-propenoxy)phenol
e. 4-(1-methylpentoxy)phenol
f. 4-(1,3-dimethylbutoxy)phenol

II a. 2-[4-(3-methyl-2-butenoxy)phenoxy]ethyl N-ethylcarbamate
b. 2-[4-(1-methylbutoxy)phenoxy]ethyl N-ethylcarbamate
c. 2-[4-(2-methylbutoxy)phenoxy]ethyl N-ethylcarbamate
d. 2-[4-(2-chloro-2-propenoxy)phenoxy]ethyl N-ethylcarbamate
e. 2-[4-(1-methylpentoxy)phenoxy]ethyl N-ethylcarbamate
f. 2-[4-(1,3-dimethylbutoxy)phenoxy]ethyl N-ethylcarbamate Again following the procedures of Example 1, each of the above N-ethylcarbamates is reacted with methyloxalyl chloride to give the corresponding N-ethyl-N-methoxalylcarbamates as final products.

EXAMPLE 5

To sodium hydride (0.15 g, 6.0 mmol), prewashed with pentane, in 5 ml of DMF and cooled in an ice bath, is added 2-[4-(1-methylpropoxy)phenoxy]ethanol (1.26 g, 6.0 mmol) in 5 ml of DMF. The mixture is stirred for 20 min. at ca. 5°, after which it is heated to 50° for 20 min. The mixture is again cooled to ca. 5° and ethyl isothiocyanate (0.58 ml, 6.0 mmol) and 5 ml DMF are added. After 1 hour at 5°, the mixture is allowed to warm to RT, and any residual sodium hydride is destroyed by addition of 2 drops of methanol The reaction mixture is poured into water and acidified with 3N-sulfuric acid. The aqueous phase is extracted with ether (3X), and the combined organic phases are washed with water, with 10% sodium bicarbonate, with water and with brine, dried and filtered and the filtrate is concentrated in vacuo to give, after purification by prep. TLC, O-2-[4-(1-methylpropoxy)phenoxy]ethyl N-ethylthiocarbamate.

Following the procedure of Example 1, methyloxalyl chloride and O-2-[4-methylpropoxy)phenoxy]ethyl N-ethylthiocarbamate are reacted together to give O-2-[4-(1-methylpropoxy)phenoxy]ethyl N-ethyl-N-methoxalylthiocarbamate (compound 4, Table A).

EXAMPLE 6

A mixture of hydroquinone (11.0 g, 100.0 mmol), ethyl 2-chloroethylcarbamate (7.6 g, 50.0 mmol) and potassium carbonate (13.8 g, 100.0 mmol) in 100 ml of dimethylformamide (DMF) is heated at 80° for 20 hours. After cooling to RT, the reaction mixture is poured into ice water and hexane, and the hexane layer is discarded to remove the bis ether by-product. The aqueous layer is then extracted with ether (3X) and the combined ether layers are washed with water, followed with brine, and dried over calcium sulfate. The solvent is removed and the residue is diluted with chloroform to precipitate out the excess hydroquinone. Following filtration, the filtrate is collected and rotoevaporated to give ethyl N-[2-(4-hydroxyphenoxy)ethyl]carbamate, a solid.

To pre-washed sodium hydride (0.106 g, 4.4 mmol) in 5 ml of tetrahydrofuran (THF) and 5 ml of DMF at RT is added ethyl N-[2-(4-hydroxyphenoxy)ethyl]carbamate (1.0 g, 4.4 mmol) in 5 ml of THF. The mixture is stirred at RT for 1.5 hours and is then cooled to −5°. 1-Methylpropyl bromide (0.72 g, 5.3 mmol) in 2 ml of THF is added to the mixture, followed by addition of 5 ml of DMF. The reaction mixture is allowed to warm slowly to RT, and is then heated at 60° for 18 hours. The reaction is cooled to RT and poured into water, and the mixture is extracted with ether (3X). The combined ether layers are washed with water until neutral, followed with brine, and dried over calcium sulfate. The solvent is removed in vacuo and purification by prep. TLC yields ethyl N-{2-[4-(1-methylpropoxy)phenoxy]ethyl}carbamate.

Following the procedure of Example 1, methyloxalyl chloride (1.10 ml, 11.70 mmol) and the above carbamate (2.04 g, 7.30 mmol) and the above carbamate (2.04 g, 7.30 mmol) are reacted together to yield ethyl N-methoxalyl-N-{2-[4-(1-methylpropoxy)phenoxy]ethyl} carbamate, MS m/e 368 (M+ +H) (compound 1, Table B).

nmr (CDCl$_3$) δ centered at 0.97 (m, 3H), centered at 1.26 (d, 3H), 3.90 (s, 3H), centered at 4.12 (m, 4H), centered at 4.32 (q, 2H) and 6.82 ppm (s, 4H).

EXAMPLE 7

To a mixture of 2-[4-(1-methylpropylthio)phenoxy]ethanol (4.26 g, 20.0 mmol) and triethylamine (4.2 ml, 30.0 mmol) in 100 ml methylene chloride at 0° is added dropwise methanesulfonyl chloride (1.7 ml, 22.0 mmol). The mixture is stirred at 0° for 20 min, after which it is poured into ice water. The methylene chloride layer is washed with ice water, with cold 10% sulfuric acid, with cold 5% sodium bicarbonate and with cold brine, dried and the solvent removed to give 2-[4-(1-methylpropylthio)phenoxy]ethylmethanesulfonate.

The above sulfonate (5.76 g, 20.0 mmol) is added dropwise to a mixture of phthalimide (3.70 g, 25.0 mmol) and potassium carbonate (4.10 g, 30.0 mmol) in 50 ml of DMF and under N$_2$. The resulting mixture is heated to 60° for 9 hours, with stirring, and is then stirred at 40° overnight. After cooling, water is added to the reaction mixture and the aqueous phase is extracted with ether (3X). The combined organic layers are washed with water and with brine, dried and rotoevaporated to give N-{2-[4-(1-methylpropylthio)phenoxy]ethyl}phthalimide.

To a solution of the above phthalimide (6.84 g, 19.7 mmol) in 100 ml of ethanol, heated to 60°, is added hydrazine hydrate (2.0 ml, 41.0 mmol) with stirring. Additional ethanol (100 ml) is added and the mixture is stirred overnight at 60°. After cooling, 5% sodium hydroxide is added and the basic mixture is extracted with ether. The combined organic layers are washed with water and brine, dried and rotoevaporated to give 2-[4-(1-methylpropylthio)phenoxy]ethylamine.

To a solution of the above amine (2.41 g, 10.0 mmol) in 10 ml DMF, cooled to 0° and under N$_2$, is added potassium carbonate (1.66 g, 12.0 mmol) followed by dropwise addition of ethyl chloroformate (1.2 ml, 12.0 mmol) in 5 ml of DMF. After 1.5 hours, water is added and the aqueous phase is extracted with ether. The combined organic layers are washed with water and brine, dried, rotoevaporated and the residue is purified by column chromatography to give ethyl N-{2-[4-(1-methylpropylthio)phenoxy]ethyl}carbamate.

Following the procedure of Example 1, methyloxalyl chloride and the above carbamate are reacted together to give ethyl N-methoxalyl-N-{2-[4-(1-methylpropylthio)phenoxy]ethyl}carbamate (compound 2, Table B).

EXAMPLE 8

To 4-(1-methylpropoxy)phenol (44.3 mmol) in 25 ml of DMF is added, under N$_2$, potassium carbonate (51.0 mmol) followed by dropwise addition of N-(bromoethyl)phthalimide (51.0 mmol) in 30 ml of DMF. The mixture is stirred at RT overnight. Water is then added and the aqueous phase is extracted with ether. The combined organic layers are washed with 5% sodium hydroxide, with water and with brine, dried and the solent removed to give N-{2-[4-(1-methylpropoxy)phenoxy]ethyl}phthalimide. Following the procedures of Example 7, the above phthalimide (5.7 mmol) is reacted with hydrazine hydrate (5.7 mmol) to give 2-[4-(1-methylpropoxy)phenoxy]ethylamine.

Following the procedures of Example 7, the above amine is reacted with S-ethyl chlorothioformate to give S-ethyl N-2-[4-(1-methylpropoxy)phenoxy]ethyl thiocarbamate.

Following the procedures of Example 1, methyl oxalyl chloride and the above carbamate are reacted together to give S-ethyl N-methoxalyl-N-{2-[4-(1-methylpropoxy)phenoxy]ethyl}thiocarbamate, MS m/e 384 (M+ +H) (compound 3, Table B).

nmr (CDCl$_3$) δ centered at 1.13 (m, 9H), centered at 3.02 (q, 2H), 3.91 (s, 3H), centered at 4.15 (m, 4H), and 6.83 ppm (s, 4H).

EXAMPLE 9

To a solution of 4.04 g (10.0 mmol) of Lawwesson's reagent [2,4-bis(4-methoxyphenyl)-1,3-diatha-2,4-diphosphetane-2,4-disulfide] in 100 ml of toluene under reflux is added ethyl N-2-[4-(1-methylpropoxy)phenoxy]ethyl carbamate (2.81 g, 10.0 mmol) in 10 ml of toluene. The reaction mixture is heated under reflux overnight, after which it is allowed to cool to RT and then poured into water. The resulting organic phase is washed with 5% sodium bicarbonate, with 10% sulfuric acid, with water and with brine, dried and filtered. The solvent is removed by rotoevaporation to give a solid which is rinsed with acetone. The acetone is evaporated off, and the resulting brown oil is purified by column chromatography to give O-ethyl N-{2-[4-(1-methylpropoxy)phenoxy]ethyl}thiocarbamate.

The above carbamate is reacted with methyl oxalyl chloride, following Example 1 procedures, to give Q-ethyl N-methoxalyl-N-{2-[4-(1-methylpropoxy)phenoxy]ethyl}thiocarbamate (compound 4, Table B).

EXAMPLE 10

To a solution of 4-(1-methylpropoxy)phenol (1.58 g, 9.5 mmol) in 10 ml of DMF at 50° is added potassium carbonate (3.90 g, 28.0 mmol). To this is added dropwise methyl 2-bromopropionate (3.2 ml, 30.0 mmol) in 10 ml of DMF. The mixture is stirred at 70° for 60 hours. The cooled reaction is worked up by addition of water and extraction with a mixture of ether/hexane (3X). The combined organic extracts are washed with 10% sulfuric acid, with water and with brine, dried and the solvent removed to give methyl 2-[4-(1-methylpropoxy)phenoxy]propanoate.

To the above propanoate (2.52 g, 7.4 mmol) in 25 ml of methanol at 0° is added 10 ml of conc. ammonium hydroxide. The reaction mixture is allowed to warm to RT and is stirred at RT overnight. The methanol is removed by rotoevaporation and the aqueous portion is filtered to give methyl 2-[4-(1-methylpropoxy)phenoxy]propanamide, a white solid.

To the above propanamide (1.32 g, 5.6 mmol) in 10 ml of THF at 0° is added dropwise 0.97M BH$_3$-THF (35 ml) over 40 min. The solution is heated under reflux overnight and is then allowed to sit at RT for 48 hours, after which 10 ml of water is added dropwise over 30 min., followed by dropwise addition of 20 ml of aqueous 5N HCl. The THF is removed by distillation, and the aqueous phase is saturated with NaOH pellets and extracted with ether (3X). The combined organic layers are washed with water and with brine, dried and solvent removed to give 2-[4-(1-methylpropoxy)phenoxy]propylamine.

To a solution of 2-[4-(1-methylpropoxy)phenoxy]-propylamine (1.13 g, 5.10 mmol) in 25 ml of ether, at 0° and under N$_2$, is added ethyl chloroformate (1.16 g, 10.60 mmol) by syringe, followed by addition of 10% aqueous sodium hydroxide (3.4 ml). After 15 min., the reaction is worked up by addition of water and extraction with ether. The combined organic phases are washed with 1N sulfuric acid, with water and with brine, dried and filtered, the filtrate is concentrated in vacuo and the product is purified by prep. TLC to give ethyl N-{2-[4-(1-methylpropoxy)phenoxy]propyl}carbamate.

The above carbamate is reacted with methyl oxalyl chloride, following Example 1 procedures, to give ethyl N-methoxalyl-N-{2-[4-(1-methylpropoxy)phenoxy]propyl}carbamate, MS m/e 382 (M$^+$ +H).

nmr (CDCl$_3$) δ centered at 1.10 (m, 12H), 3.88 (s, 3H) and 6.82 ppm (s, 4H).

EXAMPLE 11

Following the procedures of Example 6, each of the halides under column III is reacted with ethyl N-[2-(4-hydroxyphenoxy)ethyl]carbamate to give the corresponding carbamate under column IV.

III a. 3-methyl-2-butenyl bromide
b. 1-methylbutyl bromide
c. 2-methylbutyl bromide
d. 2-chloro-2-propenyl bromide
e. 1-methylpentyl chloride
f. 1,3-dimethylbutyl bromide

IV a. ethyl N-{2-[4-(3-methyl-2-butenoxy)phenoxy]ethyl} carbamate
b. ethyl N-{2-[4-(1-methylbutoxy)phenoxy]ethyl}carbamate
c. ethyl N-{2-[4-(2-methylbutoxy)phenoxy]ethyl}carbamate
d. ethyl N-{2-[4-(2-chloro-2-propenoxy)phenoxy]ethyl} carbamate
e. ethyl N-{2-[4-(1-methylpentoxy)phenoxy]ethyl}carbamate
f. ethyl N-{2-[4-(1,3-dimethylbutoxy)phenoxy]ethyl} carbamate Following the procedures of Example 1, each of the above carbamates under column IV is reacted with methyl oxalyl chloride to yield the corresponding N-methoxalylcarbamates as final products.

EXAMPLE 12

A mixture of 4-(1-methylpropoxy)phenol (9.2 mmol), methyl 2-chloroethylcarbamate (11.9 mmol), and potassium carbonate (18.4 mmol) in 20 ml of dimethylformamide (DMF) is heated at 85° for 18 hours. The reaction mixture is cooled to room temperature (RT), poured into water and extracted with ether. The combined ether extracts are washed with water until neutral, followed with brine and dried over calcium sulfate. The solvent is removed in vacuo and the residue is placed under high vacuum at 80° for ca. 2 hours to remove the excess methyl 2-chloroethylcarbamate. Purification by preparative thin layer chromatography (prep. TLC) gives methyl N-{2-[4-(1-methylpropoxy)phenoxy]ethyl}carbamate.

Following Example 1 procedures, methyloxalyl chloride and methyl N-2-[4-(1-methylpropoxy)phenoxy]ethyl carbamate are reacted together to give methyl N-methoxalyl-N-{2-[4-(1-methylpropoxy)phenoxy]ethyl}carbamate.

EXAMPLE 13

Following the procedure of Example 1, 2-[4-(1-methylpropoxy)phenoxy]ethyl N-ethylcarbamate is reacted with each of the halides or anhydrides under column V to give the corresponding final product in Table A.

V 5. acetic formic anhydride
6. acetic anhydride
7. trifluoroacetic anhydride
8. methyl chloroformate
9. ethyl chloroformate
10. methyl chlorothioformate
11. pyruvyl chloride
12. oxalyl chloride; then water
13. ethoxalyl chloride
14. isopropyl oxalyl chloride
15. t-butyl oxalyl chloride
16. n-pentyl oxalyl chloride
17. phenyl oxalyl chloride
18. 4-chlorophenyl oxalyl chloride
19. ethyl malonyl bromide
20. methyl glutaryl chloride
21. dimethoxyphosphinyl chloride
22. dimethoxyphosphinothioyl chloride Following the same procedures, each of the halides above under column V is reacted with ethyl N-{2-[4-(1-methylpropoxy)phenoxy]ethyl}carbamate to give the corresponding final product in Table B.

EXAMPLE 14

To O-2-[4-(1-methylpropoxy)phenoxy]ethyl N-ethylcarbamate (1.50 g, 5.34 mmol) and pyridine (1 ml, 11.75 mmol) in 20 ml of methylene chloride at RT is added phenylsulfenyl chloride (1.54 g, 10.70 mmol). The reaction mixture is stirred for 2 hours, after which it is poured into ice water and extracted with ether. The combined organic layers are washed with 10% HCl, with water until neutral and with brine and dried. After filtration and removal of the solvent, the product is purified by prep. TLC to give O-2-[4-(1-methylpropoxy)phenoxy]ethyl N-ethyl-N-phenylsulfenylcarbamate, MS m/e 390 (M$^+$ +H) (compound 23, Table A).

nmr (CDCl$_3$) δ centered at 1.08 (m, 9H), centered at 3.65 (q, 2H), centered at 4.17 (m, 3H), centered at 4.50 (m, 2H), 6.80 (s, 4H) and 7.25 ppm (s, 5H).

Following the above procedures ethyl N-2-[4-(1-methylpropoxy)phenoxy]ethyl carbamate and phenylsulfenyl chloride are reacted together to give ethyl N-phenylsulfenyl-N-{2-[4-(1-methylpropoxy)phenoxy]ethyl}carbamate, MS m/e 390 (M$^+$ +H) (compound 23, Table B).

nmr (CDCl$_3$) δ centered at 1.13 (m, 9H), centered at 4.23 (m, 7H), 6.82 (s, 4H) and 7.32 ppm (s, 5H).

EXAMPLE 15

Following the procedure of Example 14, 2-[4-(1-methylpropoxy)phenoxy]ethyl N-ethylcarbamate is reacted with each of the halides under column VI to give the corresponding final product in Table A.

VI 24. 4-chlorophenylsulfenyl chloride
25. 3-trifluoromethylphenylsulfenyl chloride
26. 4-chloro-3-trifluoromethylphenylsulfenyl chloride
27. 2-toluenesulfenyl chloride
28. 2-toluenesulfinyl chloride
29. 2-toluenesulfonyl chloride
30. 1-cyano-1-methylethanesulfenyl chloride
31. N,N-di-n-butylaminosulfenyl chloride
32. N-isopropyl-N-ethoxycarbonylethylaminosulfenyl chloride
33. N-methyl-N-n-butoxycarbonylaminosulfenyl chloride
34. N-methyl-N-methoxycarbonylaminosulfenyl chloride
35. N-methyl-N-ethoxycarbonylaminosulfenyl chloride
36. N-methyl-N-pentoxycarbonylaminosulfenyl chloride
37. N-methyl-N-heptoxycarbonylaminosulfenyl chloride
38. N-methyl-N-decoxycarbonylaminosulfenyl chloride Following the same procedures, each of the halides under column VI is reacted with ethyl N-{2-[4-(1-methylpropoxy)phenoxy]ethyl}carbamate to give the corresponding final product in Table B.

EXAMPLE 16

To a mixure of O-2-[4-(1-methoxypropoxy)phenoxy]ethyl N-ethylcarbamate (4.21 g, 15.0 mmol) and pyridine (1.95 ml, 24.0 mmol) in methylene chloride (10 ml) at reflux is added freshly distilled sulfur dichloride (0.93 g, 9.0 mmol). Following addition, the reaction mixture is heated under reflux for 0.5 hr and is then cooled to RT. Additional methylene chloride is added to the mixture and the mixture is washed with water, with 5% aqueous sodium bicarbonate solution, with additional water and with brine, dried over calcium sulfate and filtered. The solvent is removed from the filtrate under reduced pressure and the crude residue is purified by prep. TLC to give bis{[4-(1-methylpropoxy)phenoxyethyl]-N-ethyl carbamyl}sulfide.

TABLE A $$CH_3-CH_2-CH(CH_3)-W^1-\text{C}_6H_4-O-CH_2-CH_2-X-\overset{Y}{\underset{\parallel}{C}}-N(R^7)-CH_2-CH_3$$

| Cpd | $W^1$ | X | Y | $R^7$ |
|---|---|---|---|---|
| 1 | O | O | O | $-C(=O)-C(=O)-O-CH_3$ |
| 2 | S | O | S | $-C(=O)-C(=O)-O-CH_3$ |
| 3 | S | O | O | $-C(=O)-C(=O)-O-CH_3$ |
| 4 | O | O | S | $-C(=O)-C(=O)-O-CH_3$ |
| 5 | O | O | O | $-CH$ |
| 6 | O | O | O | $-C(=O)-CH_3$ |
| 7 | O | O | O | $-C(=O)-CF_3$ |
| 8 | O | O | O | $-C(=O)-O-CH_3$ |
| 9 | O | O | O | $-C(=O)-OCH_2-CH_3$ |
| 10 | O | O | O | $-C(=O)-S-CH_3$ |
| 11 | O | O | O | $-C(=O)-C(=O)-CH_3$ |
| 12 | O | O | O | $-C(=O)-C(=O)-OH$ |
| 13 | O | O | O | $-C(=O)-C(=O)-O-CH_2CH_3$ |
| 14 | O | O | O | $-C(=O)-C(=O)-O-CH(CH_3)_2$ |
| 15 | O | O | O | $-C(=O)-C(=O)-O-C(CH_3)_3$ |
| 16 | O | O | O | $-C(=O)-C(=O)-O-(CH_2)_4CH_3$ |
| 17 | O | O | O | $-C(=O)-C(=O)-O-C_6H_5$ |
| 18 | O | O | O | $-C(=O)-C(=O)-O-C_6H_4-Cl$ |
| 19 | O | O | O | $-C(=O)-CH_2-C(=O)-O-CH_2CH_3$ |
| 20 | O | O | O | $-C(=O)-(CH_2)_3-C(=O)-O-CH_3$ |
| 21 | O | O | O | $-P(=O)(OCH_3)_2$ |
| 22 | O | O | O | $-P(=S)(OCH_3)_2$ |

TABLE A-continued $$CH_3-CH_2-CH(CH_3)-W^1-\text{C}_6H_4-O-CH_2-CH_2-X-C(=Y)-N(R^7)-CH_2-CH_3$$

| Cpd | W¹ | X | Y | R⁷ |
|---|---|---|---|---|
| 23 | O | O | O | S—C₆H₅ |
| 24 | O | O | O | S—C₆H₄—Cl (4-) |
| 25 | O | O | O | S—C₆H₄—CF₃ (3-) |
| 26 | O | O | O | S—C₆H₃(CF₃)(Cl) (3-CF₃, 4-Cl) |
| 27 | O | O | O | S—C₆H₄—CH₃ (2-) |
| 28 | O | O | O | S(=O)—C₆H₄—CH₃ |
| 29 | O | O | O | S(=O)₂—C₆H₄—CH₃ |
| 30 | O | O | O | S—C(CH₃)₂—CN |
| 31 | O | O | O | S—N(CH₂CH₂CH₂CH₃)₂ |
| 32 | O | O | O | S—N(CH(CH₃)₂)—CH₂—CH₂—C(=O)—O—CH₂CH₃ |
| 33 | O | O | O | S—N(CH₃)—C(=O)—O—(CH₂)₃CH₃ |
| 34 | O | O | O | S—N(CH₃)—C(=O)—O—CH₃ |
| 35 | O | O | O | S—N(CH₃)—C(=O)—O—CH₂CH₃ |
| 36 | O | O | O | S—N(CH₃)—C(=O)—O—(CH₂)₄CH₃ |
| 37 | O | O | O | S—N(CH₃)—C(=O)—O—(CH₂)₆CH₃ |
| 38 | O | O | O | S—N(CH₃)—C(=O)—O—(CH₂)₉CH₃ |

TABLE B $$CH_3-CH_2-CH(CH_3)-W^1-\text{C}_6H_4-O-CH_2-CH_2-N(R^7)-C(=Y)-X^1-CH_2-CH_3$$

| Cpd | W¹ | Y | X¹ | R⁷ |
|---|---|---|---|---|
| 1 | O | O | O | C(=O)—C(=O)—O—CH₃ |
| 2 | S | O | O | C(=O)—C(=O)—O—CH₃ |
| 3 | O | O | S | C(=O)—C(=O)—O—CH₃ |
| 4 | O | S | O | C(=O)—C(=O)—O—CH₃ |
| 5 | O | O | O | CH(=O) |
| 6 | O | O | O | C(=O)—CH₃ |
| 7 | O | O | O | C(=O)—CF₃ |
| 8 | O | O | O | C(=O)—O—CH₃ |
| 9 | O | O | O | C(=O)—O—CH₂—CH₃ |
| 10 | O | O | O | C(=O)—S—CH₃ |
| 11 | O | O | O | C(=O)—C(=O)—CH₃ |
| 12 | O | O | O | C(=O)—C(=O)—OH |
| 13 | O | O | O | C(=O)—C(=O)—O—CH₂CH₃ |
| 14 | O | O | O | C(=O)—C(=O)—O—CH(CH₃)₂ |

TABLE B-continued $$CH_3-CH_2-W^1-\bigcirc-O-CH_2-CH_2-N-\overset{Y}{\underset{\|}{C}}-X^1-CH_2-CH_3$$
$$\underset{CH_3}{|} \quad \underset{R^7}{|}$$

| Cpd | W¹ | Y | X¹ | R⁷ |
|---|---|---|---|---|
| 15 | O | O | O | −C(=O)−C(=O)−O−C(CH₃)₃ |
| 16 | O | O | O | −C(=O)−C(=O)−O−(CH₂)₄CH₃ |
| 17 | O | O | O | −C(=O)−C(=O)−O−C₆H₅ |
| 18 | O | O | O | −C(=O)−C(=O)−O−C₆H₄−Cl |
| 19 | O | O | O | −C(=O)−CH₂−C(=O)−O−CH₂CH₃ |
| 20 | O | O | O | −C(=O)−(CH₂)₃−C(=O)−O−CH₃ |
| 21 | O | O | O | −P(=O)(OCH₃)₂ |
| 22 | O | O | O | −P(=S)(OCH₃)₂ |
| 23 | O | O | O | −S−C₆H₅ |
| 24 | O | O | O | −S−C₆H₄−Cl |
| 25 | O | O | O | −S−C₆H₄−CF₃ (meta) |
| 26 | O | O | O | −S−C₆H₃(CF₃)(Cl) |
| 27 | O | O | O | −S−C₆H₄−CH₃ |
| 28 | O | O | O | −S(=O)−C₆H₄−CH₃ |
| 29 | O | O | O | −S(=O)₂−C₆H₄−CH₃ |
| 30 | O | O | O | S−C(CH₃)₂−CN |
| 31 | O | O | O | S−N(CH₂CH₂CH₂CH₃)₂ |
| 32 | O | O | O | −S(=O)−N(CH(CH₃)₂)−CH₂−CH₂−C(=O)−O−CH₂CH₂ |
| 33 | O | O | O | −S−N(CH₃)−C(=O)−O(CH₂)₃CH₃ |
| 34 | O | O | O | −S−N(CH₃)−C(=O)−O−CH₃ |
| 35 | O | O | O | −S−N(CH₃)−C(=O)−O−CH₂CH₃ |
| 36 | O | O | O | −S−N(CH₃)−C(=O)−O−(CH₂)₄CH₃ |
| 37 | O | O | O | −S−N(CH₃)−C(=O)−O−(CH₂)₆CH₃ |
| 38 | O | O | O | −S−N(CH₃)−C(=O)−O−(CH₂)₉CH₃ |

What is claimed is:

1. A compound of the following formula (A):

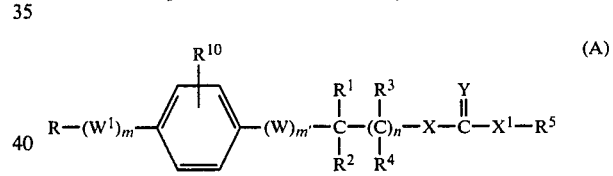

(A)

wherein,
each of m and m' is independently zero or one;
n is zero, one, two or three;
n' is zero, one or two;
n" is zero, one, two or three;
W is oxygen, sulfur, NR⁶, CR³R⁴ or carbonyl;
W¹ is oxygen, sulfur, NR⁶, CR³R⁴, carbonyl, sulfinyl or sulfonyl;
each of X and X¹ is oxygen, sulfur or NR⁷; provided that one of X or X¹ must be NR⁷, while the other of X or X¹ is oxygen or sulfur;
X² is oxygen or sulfur;
Y is oxygen, or sulfur;
Z is oxygen or sulfur;
R is hydrogen, lower alkyl, lower alkenyl, lower alkynyl, lower haloalkyl, lower haloalkenyl, lower haloalkynyl, lower alkoxyalkyl, lower alkylthioalkyl, cycloalkyl, halocycloalkyl, or cycloalkylalkyl,
each of R¹, R², R³, R⁴, and R⁶ is independently hydrogen or lower alkyl;
R⁵ is lower alkyl, lower alkenyl, lower alkynyl, lower haloalkyl, lower haloalkenyl, lower haloalkynyl, cycloalkyl, cyaloalkylalkyl, phenyl or substituted phenyl;
R⁷ is selected from the groups:

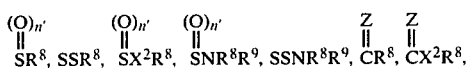
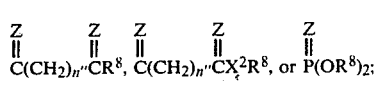

$R^8$ is hydrogen, lower alkyl, lower haloalkyl, lower cycnoalkyl, or substituted or unsubstituted aryl;

$R^9$ is lower alkyl, aryl, alkoxycarbonyl, substituted or unsubstituted aryloxycarbonyl, alkoxycarbonylalkyl, lower alkylsulfonyl, alkylaminosulfonyl, dialkylaminosulfonyl or the group

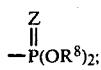

and $R^{10}$ is hydrogen, lower alkyl, lower haloalkyl or halogen.

2. A compound of the following formula, according to claim 1:

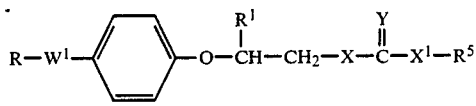

wherein, $W^1$ is oxygen or sulfur; R is lower alkyl, lower alkenyl, lower alkoxyalkyl or lower haloalkyl; $R^1$ is hydrogen or methyl; and $R^5$ is lower alkyl of 1 to 4 carbon atoms.

3. A compound according to claim 2 wherein X is oxygen or sulfur, $X^1$ is $NR^7$ and Y is oxygen or sulfur.

4. A compound according to claim 3 wherein X is oxygen.

5. A compound according to claim 4 wherein R is 1-methylpropyl, 1-methylbutyl, 1,3-dimethylbutyl or 3-methyl-2-butenyl.

6. A compound according to claim 2 wherein X is $NR^7$, $X^1$ is oxygen or sulfur and Y is oxygen or sulfur.

7. A compound according to claim 6 wherein $X^1$ is oxygen.

8. A compound according to claim 7 wherein R is 1-methylpropyl, 1-methylbutyl, 1,3-dimethylbutyl or 3-methyl-2-butenyl.

9. A compound of the following formula, according to claim 2:

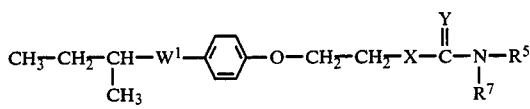

wherein, X is oxygen or sulfur and Y is oxygen or sulfur.

10. A compound according to claim 9 wherein $R^5$ is methyl or ethyl and $R^7$ is the group

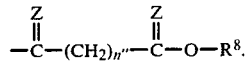

11. A compound according to claim 10 wherein $R^8$ is hydrogen, substituted or unsubstituted phenyl or lower alkyl and Z is oxygen.

12. The compound O-2-[4-(1-methylpropoxy)phenoxy]ethyl N-ethyl-N-methoxalylcarbamate, according to claim 11.

13. The compound O-2-[4-(1-methylpropylthio)phenoxy]ethyl N-ethyl-N-methoxalylcarbamate, according to claim 11.

14. The compound O-2-[4-(1-methylpropylthio)phenoxy]ethyl N-ethyl-N-methoxaylthiocarbamate, according to claim 11.

15. A compound according to claim 9 wherein $R^5$ is methyl or ethyl and $R^7$ is the group $-SR^8$ or $-SNR^8R^9$.

16. A compound according to claim 15 wherein $R^8$ is lower alkyl, phenyl or substituted phenyl and $R^9$ is lower alkyl, alkoxycarbonyl or alkoxycarbonylalkyl.

17. The compound O-2-[4-(1-methylpropoxy)phenoxy]ethyl N-ethyl-N-phenylsulfenylcarbamate, according to claim 16.

18. A compound of the following formula, according to claim 2:

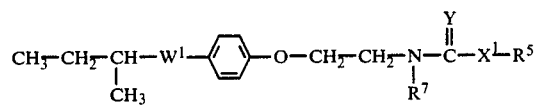

wherein, $X^1$ is oxygen or sulfur and Y is oxygen or sulfur.

19. A compound according to claim 18 wherein $R^5$ is methyl or ethyl and $R^7$ is the group

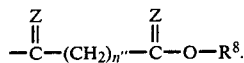

20. A compound according to claim 19 wherein $R^8$ is hydrogen, substituted or unsubstituted phenyl or lower alkyl and Z is oxygen.

21. The compound ethyl N-methoxalyl-N-{2-[4-(1-methylpropoxy)phenoxy]propyl}carbamate, according to claim 20.

22. The compound ethyl N-methoxalyl-N-{2-[4-(1-methylpropoxy)phenoxy]ethyl}carbamate, according to claim 20.

23. The compound S-ethyl N-methoxalyl-N-{2-[4-(1-methylpropoxy)phenoxy]ethyl}thiocarbamate, according to claim 20.

24. A compound according to claim 18 wherein $R^5$ is methyl or ethyl and $R^7$ is the group $-SR^8$ or $-SNR^8R^9$.

25. A compound according to claim 24 wherein $R^8$ is lower alkyl, phenyl or substituted phenyl and $R^9$ is lower alkyl, alkoxycarbonyl or alkoxycarbonylalkyl.

26. The compound ethyl N-phenylsulfenyl-N-{2-[4-(1-methylpropoxy)phenoxy]ethyl}carbamate, according to claim 25.

* * * * *